United States Patent
Shima et al.

(10) Patent No.: US 11,058,386 B2
(45) Date of Patent: Jul. 13, 2021

(54) X-RAY DIAGNOSIS APPARATUS AND MEDICAL IMAGE DIAGNOSIS SYSTEM FOR SPECIFYING A DEVICE BEING CURRENTLY OPERATED

(71) Applicant: TOSHIBA MEDICAL SYSTEMS CORPORATION, Otawara (JP)

(72) Inventors: Kazunari Shima, Nasushiobara (JP); Hajime Yoshida, Nasushiobara (JP); Kazuhiro Taniyama, Otawara (JP); Satoru Ohishi, Otawara (JP); Takeo Matsuzaki, Nasushiobara (JP)

(73) Assignee: CANON MEDICAL SYSTEMS CORPORATION, Otawara (JP)

( * ) Notice: Subject to any disclaimer, the term of this patent is extended or adjusted under 35 U.S.C. 154(b) by 1144 days.

(21) Appl. No.: 15/351,923

(22) Filed: Nov. 15, 2016

(65) Prior Publication Data
US 2017/0135662 A1 May 18, 2017

(30) Foreign Application Priority Data

Nov. 16, 2015 (JP) .............................. JP2015-223977
Nov. 14, 2016 (JP) .............................. JP2016-221179

(51) Int. Cl.
*A61B 6/00* (2006.01)
*A61B 34/30* (2016.01)
*A61B 34/20* (2016.01)

(52) U.S. Cl.
CPC ............ *A61B 6/5235* (2013.01); *A61B 6/466* (2013.01); *A61B 6/481* (2013.01); *A61B 6/486* (2013.01);
(Continued)

(58) Field of Classification Search
CPC ........ A61B 6/5235; A61B 6/504; A61B 6/486; A61B 6/481; A61B 6/466; A61B 6/548;
(Continued)

(56) References Cited

U.S. PATENT DOCUMENTS

2006/0258938 A1* 11/2006 Hoffman ................ A61B 34/20
  600/424
2009/0022262 A1* 1/2009 Ohishi .................... A61B 6/12
  378/4
(Continued)

FOREIGN PATENT DOCUMENTS

JP    2006-504503    2/2006
JP    2009-66396     4/2009
(Continued)

OTHER PUBLICATIONS

Japanese Office Action dated Aug. 18, 2020 in Patent Application No. 2016-221179, 7 pages.

*Primary Examiner* — Amelie R Davis
(74) *Attorney, Agent, or Firm* — Oblon, McClelland, Maier & Neustadt, L.L.P.

(57) ABSTRACT

According to one embodiment, a medical image diagnosis system includes a plurality of devices, operating circuitry, processing circuitry, and a display. The plurality of devices is to be inserted into a body of an object. The operating circuitry operates at least one of the devices. The processing circuitry obtains a medical image of the object and specifies a device being operated based on movement of the device in the medical image when the device is being operated by the operating circuitry. The display identifiably displays a device to be operated by the operating circuitry based on a result of specification by the processing circuitry.

17 Claims, 16 Drawing Sheets

(52) U.S. Cl.
CPC .............. *A61B 6/504* (2013.01); *A61B 6/548* (2013.01); *A61B 34/30* (2016.02); *A61B 2034/2065* (2016.02); *A61B 2034/301* (2016.02)

(58) Field of Classification Search
CPC . A61B 34/30; A61B 2034/301; A61B 6/4441; A61B 6/12; A61B 6/465; A61B 6/487; A61B 2034/2065
See application file for complete search history.

(56) References Cited

U.S. PATENT DOCUMENTS

| 2009/0062641 | A1 | 3/2009 | Barbu et al. | |
|---|---|---|---|---|
| 2009/0326556 | A1* | 12/2009 | Diolaiti | A61B 1/05 606/130 |
| 2010/0217116 | A1 | 8/2010 | Eck et al. | |
| 2011/0085706 | A1* | 4/2011 | Villain | A61B 6/12 382/103 |
| 2013/0216025 | A1* | 8/2013 | Chan | A61B 5/066 378/63 |

FOREIGN PATENT DOCUMENTS

| JP | 2009-519083 | 5/2009 |
|---|---|---|
| JP | 2012-81136 A | 4/2012 |
| JP | 2015-37572 | 2/2015 |
| WO | WO 2004/041347 A1 | 5/2004 |
| WO | WO 2009/137410 A1 | 11/2009 |
| WO | WO 2013/024831 A | 2/2013 |

* cited by examiner

MOVEMENT OF DEVICE TO BE OPERATED
(TWO DEVICES MOVE AT A SAME TIME)

ASSOCIATION BETWEEN DEVICE ON IMAGE
AND ACTUAL DEVICE BY COMPARING
FEEDING AMOUNT AND MOVEMENT AMOUNT
ON IMAGE

US 11,058,386 B2

X-RAY DIAGNOSIS APPARATUS AND MEDICAL IMAGE DIAGNOSIS SYSTEM FOR SPECIFYING A DEVICE BEING CURRENTLY OPERATED

CROSS-REFERENCE TO RELATED APPLICATIONS

This application claims the benefit of priority of Japanese Patent Application No. 2015-223977, filed Nov. 16, 2015, and Japanese Patent Application No. 2016-221179, filed Nov. 14, 2016, the entire contents of all of which are incorporated herein by reference.

FIELD

Embodiments described herein relate generally to an X-ray diagnosis apparatus and a medical image diagnosis system.

BACKGROUND

When catheter treatment is conducted, a user causes an X-ray radioscopic image or an X-ray radiographic image (hereinafter referred to as an X-ray image) by X-ray imaging using an X-ray diagnosis apparatus to be displayed during manipulation and carries out manipulation while checking positions of devices such as a catheter and a guide wire visualized on the X-ray image in some cases. For example, in catheter ablation, such manipulation is carried out that a portion to be treated is selectively cauterized by applying high-frequency conduction to an electrode provided at a distal end of the catheter.

For a user who carries out this type of manipulation, it is important to grasp at what position the device to be operated by the user is located on the X-ray image accurately and quickly. However, the user might lose the position of the device to be operated on the X-ray image in some cases. Moreover, when a device operation is carried out by using a remote-catheter system including a plurality of devices, if the plurality of devices are visualized on the X-ray image, it is difficult for the user to determine which device is the device to be operated on the X-ray image.

BRIEF DESCRIPTION OF THE DRAWINGS

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION

Hereinbelow, a description will be given of an X-ray diagnosis apparatus and a medical image diagnosis system according to embodiments of the present invention with reference to the drawings.

In general, according to one embodiment, a medical image diagnosis system includes a plurality of devices, operating circuitry, processing circuitry, and a display. The plurality of devices is to be inserted into a body of an object. The operating circuitry operates at least one of the devices. The processing circuitry obtains a medical image of the object and specifies a device being operated based on movement of the device in the medical image when the device is being operated by the operating circuitry. The display identifiably displays a device to be operated by the operating circuitry based on a result of specification by the processing circuitry.

First Embodiment

Figure 1:
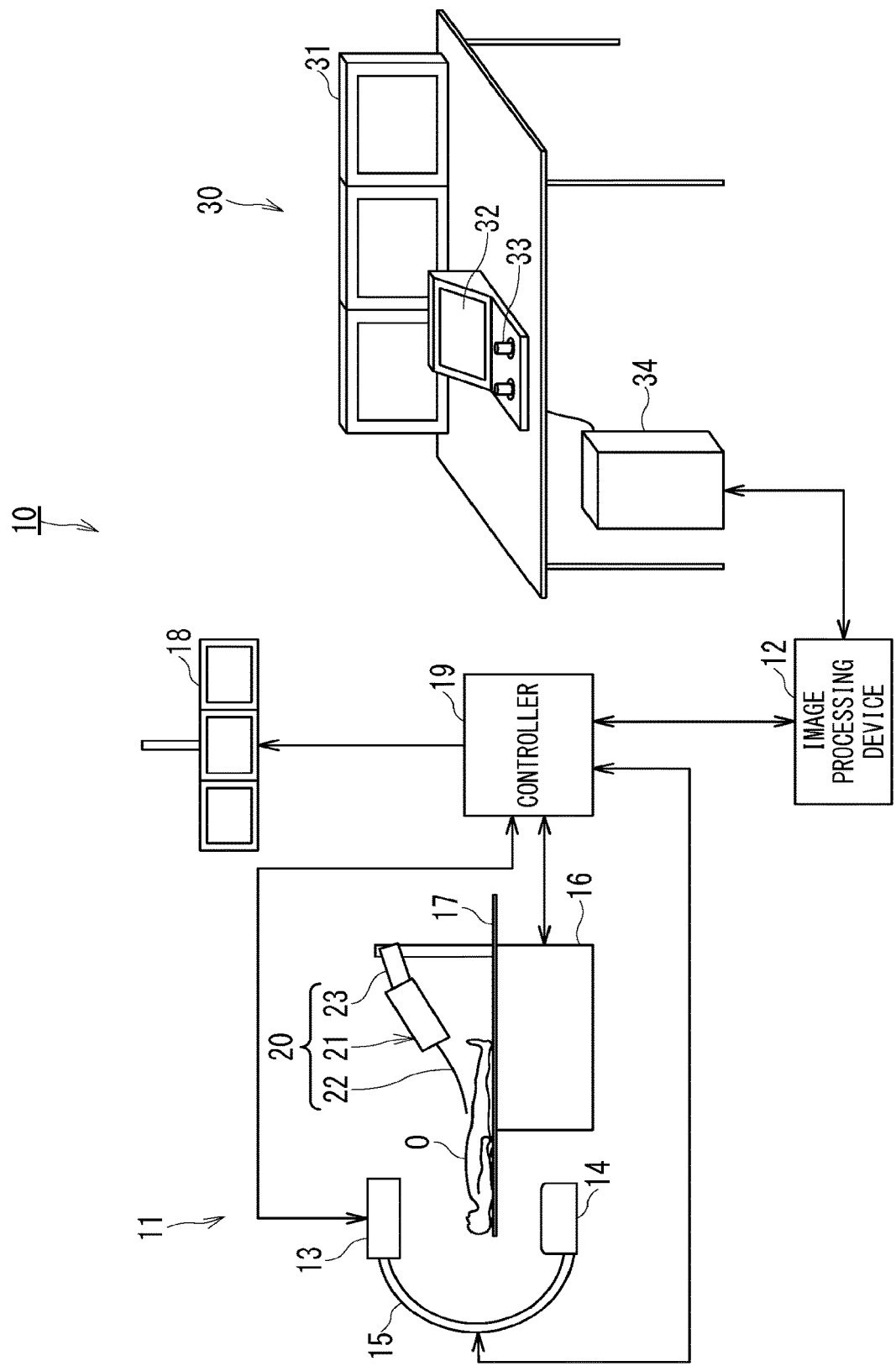
FIG. 1 is a block diagram illustrating an example of a medical image diagnosis system including an X-ray diagnosis apparatus according to a first embodiment of the present invention.

FIG. 1 is a block diagram illustrating an example of a medical image diagnosis system 10 including an X-ray diagnosis apparatus 11 according to a first embodiment of the present invention.

The X-ray diagnosis apparatus 11 is constituted as an angiography apparatus, for example, and has an image processing device 12, an X-ray detector 13, an X-ray source 14, a C-arm 15, a bed 16, a top plate 17 of the bed 16, a display 18, and a controller 19.

The X-ray detector 13 is provided on one end of the C-arm 15 so as to be arranged by facing the X-ray source 14 by sandwiching an object O supported on the top plate (a catheter table, for example) 17 of the bed 16. The X-ray detector 13 is constituted by a flat panel detector (FPD), detects an X-ray irradiated to the X-ray detector 13 through the object O and outputs projection data of the X-ray based on this detected X-ray. This projection data is given to the image processing device 12 through the controller 19. The X-ray detector 13 may include an image intensifier, a TV camera and the like.

The X-ray source 14 is provided on another end of the C-arm 15 and has an x-ray bulb and an X-ray diaphragm. The X-ray diaphragm is an X-ray irradiation field diaphragm constituted by a plurality of lead blades, for example. The X-ray diaphragm is controlled by the controller 19 and adjusts an irradiation range of the X-ray irradiated from the X-ray bulb.

The C-arm 15 integrally holds the X-ray detector 13 and the X-ray source 14. When the C-arm 15 is controlled by the controller 19 and driven, the X-ray detector 13 and the X-ray source 14 are integrally moved around the object O.

When the X-ray diagnosis apparatus 11 is used as an angiography apparatus, the X-ray diagnosis apparatus 11 may be a biplane type having two X-ray irradiation systems constituted by the X-ray detector 13, the X-ray source 14, and the C-arm 15. In a case of the biplane type, the X-ray diagnosis apparatus 11 can obtain a biplane image (an F-side image and an L-side image) by irradiating an X-ray beam individually from two directions, that is, from an F (Frontal) side having a floor-installed type C-arm and an L (Lateral) side having a ceiling-traveling type Ω-arm.

The bed 16 is installed on a floor surface and has the top plate 17. The bed 16 is controlled by the controller 19 and moves the top plate 17 in a horizontal direction and in a vertical direction.

The display 18 is constituted by one or a plurality of display regions and displays the X-ray image and the like by being controlled by the controller 19. The display 18 is constituted by a general display output device such as a liquid-crystal display, an OLED (Organic Light Emitting Diode) display and the like, for example. The X-ray image is an example of a medical image in the present application.

The controller 19 is controlled by the image processing device 12 and controls the X-ray detector 13 so as to carry out X-ray imaging of the object O and to generate projection data and gives it to the image processing device 12. The controller 19 is controlled by the image processing device 12 and generates the projection data before and after administration of a contrast agent and gives it to the image processing device 12.

If the X-ray diagnosis apparatus 11 is constituted capable of rotation DSA (Digital Subtraction Angiography) imaging, the controller 19 is controlled by the image processing device 12, carries out the rotation DSA imaging so as to generate the projection data before and after administering a contrast agent and gives it to the image processing device 12. In a case of the rotation DSA imaging, image data before the contrast agent is injected in (mask image data) and image data after the contrast agent is injected (contrast image data) of a same portion of the object O are generated, respectively. If the rotation DSA imaging can be carried out, the X-ray diagnosis apparatus 11 can also obtain a three-dimensional blood vessel image (3D blood-vessel image) on the basis of the contrast image data and the mask image obtained by the rotation DSA imaging.

The controller 19 has at least a processor and memory circuitry. The controller 19 is controlled by the image processing device 12 in accordance with a program stored in this memory circuitry and carries out X-ray imaging such as radioscopic imaging of the object O by controlling an X-ray irradiation system and outputs the projection data.

FIG. 1 illustrates an example of a case where the controller 19 and the image processing device 12 are connected via a wire, but the controller 19 and the image processing device 12 may be connected capable of data transmission/reception via a network.

The memory circuitry of the controller 19 provides a work area for temporarily storing a program executed by a processor of the controller 19 and data. Moreover, the memory circuitry of the controller 19 stores various programs and various types of data required for executing these programs. The memory circuitry of the controller 19 has constitution including a recording medium which is readable by the processor such as a magnetic or optical recording medium or a semiconductor memory and may be constituted such that a part or the whole of these programs and data in the memory circuitry are downloaded through an electronic network.

The medical image diagnosis system 10 further has a remote catheter 20 and a remote console 30. The remote catheter 20 and the remote console 30 constitute a so-called remote catheter system.

The remote catheter 20 has a robot arm 21 and a device 22, is controlled by the remote console 30 and inserts the device 22 into a predetermined portion (an affected area, for example) of the object O. Alternatively, the remote catheter 20 may have a display 23 provided on a support member constituting the robot arm 21.

Moreover, the remote catheter 20 may have an injector function and in this case, the remote catheter 20 injects the contrast agent through a catheter (a catheter tube, not shown) as the device 22. Timing of injection and stop of the contrast agent, concentration and an injecting speed of the contrast agent may be automatically controlled by the remote console 30. Alternatively, an instruction by the user may be received through a remote input circuit 33 of the remote console 30, and the contrast agent may be injected in concentration and at a speed and timing according to this instruction.

Figure 2:
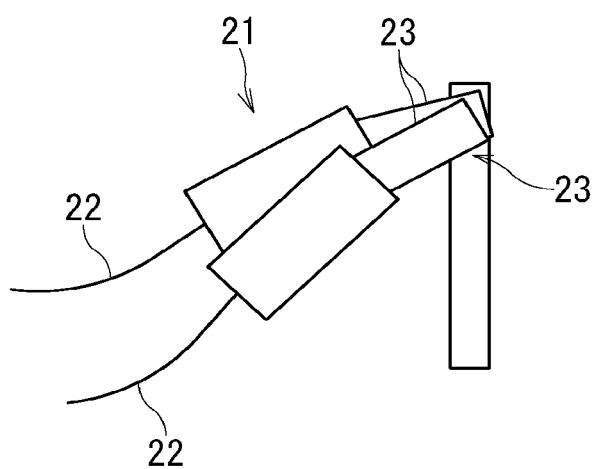
FIG. 2 is an explanatory view illustrating a constitution example of the remote catheter including the two devices.

FIG. 2 is an explanatory view illustrating a constitution example of the remote catheter 20 including the two devices 22. The remote catheter 20 is constituted capable of remote control of the plurality of devices 22.

The remote console 30 includes display input circuits 31 and 32, a remote input circuit 33 for remote control of the devices 22 of the remote catheter 20, and a control device 34.

The display input circuits 31 and 32 have a display and a touch sensor provided in a vicinity of the display. The display is constituted by a general display output device such as a liquid-crystal display, an OLED (Organic Light Emitting Diode) display and the like for example. The touch sensor gives information on an instructed position on the touch sensor by the user to processing circuitry of the control device 34. If it is constituted by an electrostatic capacity panel of a projection type, for example, the touch sensor has an electrode row arranged vertically and horizontally. In this case, the touch sensor can obtain a contact position on the basis of an output change of the electrode row according to a change in the electrostatic capacity in a vicinity of the contact position of a contact object.

The display of the display input circuit 31 is controlled by the processing circuitry of the control device 34 and displays an image similar to that on the display 18, for example.

The display of the display input circuit 32 is controlled by the processing circuitry of the control device 34 and displays information on a current device to be operated of the remote input circuit 33, for example.

The remote input circuit 33 is constituted by a general pointing device such as a track ball, a track ball mouse, a keyboard, a touch panel, a ten-key, a voice input circuit, a visual line input circuit and the like and a hand switch for instructing X-ray exposure timing and the like and outputs a signal for remote control of the devices 22 through the control device 34 to the remote catheter 20 by wire or wirelessly. The user can operate at least one of the devices 22 through the remote input circuit 33. Specifically, the user can operate the plurality of devices 22 at a same time or can selectively operate the plurality of devices 22 through the remote input circuit 33. Moreover, the medical image diagnosis system 10 may include a plurality of the remote input circuits 33. In this case, one of the plurality of remote input circuits 33 may be provided in an operation room where the X-ray diagnosis apparatus 11 is installed or may be provided in a room adjacent to the operation room or may be provided at a remote site through a network.

The control device 34 has at least a processor and memory circuitry. The processing circuitry of the control device 34 is linked with the image processing device 12 in accordance with the program stored in this memory circuitry. For example, the processing circuitry of the control device 34 gives information on a feeding movement amount of the device 22 to the image processing device 12. If there is a plurality of the devices 22, the processing circuitry of the control device 34 gives setting information on the device to be operated of the current remote input circuit 33 to the image processing device 12. The image processing device 12 controls the processing circuitry of the control device 34 so that an image in which at least a part of a device image is highlighted is displayed on at least either one of the display input circuits 31 and 32.

Figure 3:
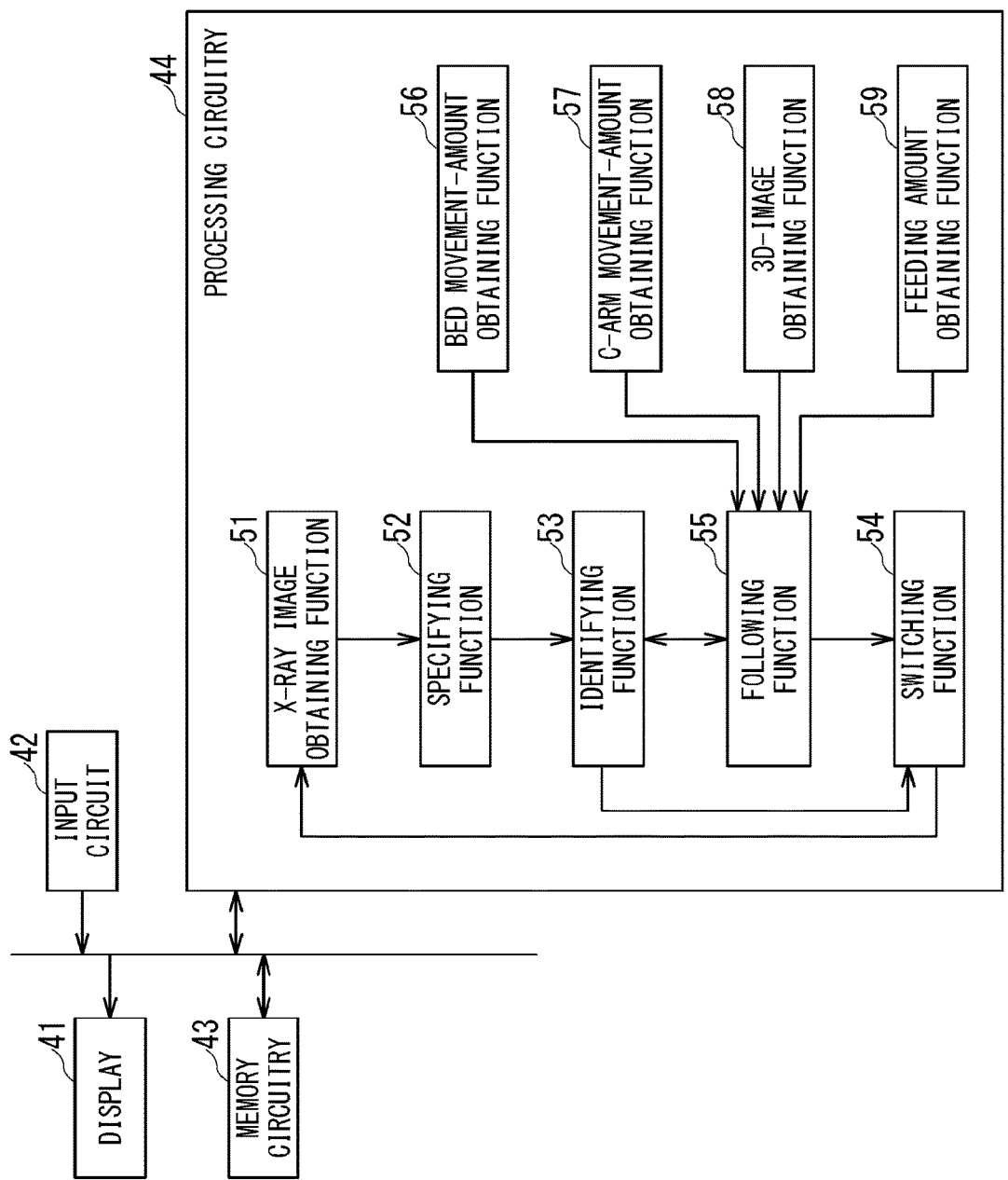
FIG. 3 is a block diagram illustrating a constitution example of the image processing device according to the first embodiment.

FIG. 3 is a block diagram illustrating a constitution example of the image processing device 12 according to the first embodiment.

The image processing device 12 has a display 41, an input circuit 42, memory circuitry 43, and processing circuitry 44.

The display 41 is constituted by a general display output device such as a liquid-crystal display, an OLED (Organic Light Emitting Diode) display and the like, for example, and displays various types of information in accordance with control of the processing circuitry 44. The input circuit 42 is constituted by a general display device such as a keyboard, a touch panel, a ten-key, a voice input circuit, a visual line input circuit and the like, for example, and outputs an operation input signal corresponding to an operation by the user to the processing circuitry 44.

The memory circuitry 43 has constitution including a recording medium such as a magnetic or optical recording medium or a semiconductor memory which is readable by a processor. A part of or the whole of the programs and data in these storage mediums may be constituted to be downloaded by communication via an electronic network.

The processing circuitry 44 is a processor for executing processing for a user to easily grasp a correspondence between each of the plurality of devices on the X-ray image and each of the plurality of devices 22 of the remote catheter system by reading out and executing the programs stored in the memory circuitry 43.

As illustrated in FIG. 3, the processing circuitry 44 realizes an X-ray image obtaining function 51, a specifying function 52, an identifying function 53, a switching function 54, a following function 55, a bed movement-amount obtaining function 56, a C-arm movement-amount obtaining function 57, a 3D-image obtaining function 58, and a feeding amount obtaining function 59. Each of these functions is stored in the memory circuitry 43 in a form of a program, respectively. Hereinafter details of an operation of each function will be described by referring to FIGS. 4 to 9.

Figure 4:
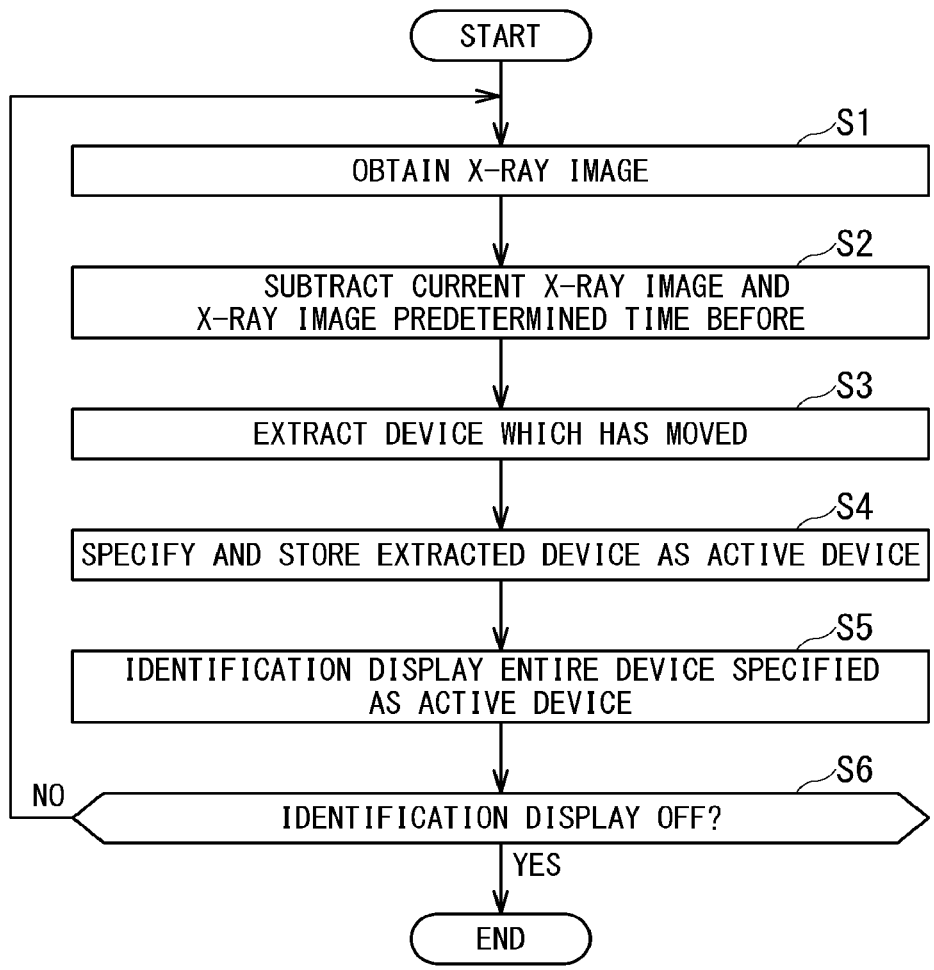
FIG. 4 is a flowchart illustrating an example of a procedure when processing for allowing the user to easily grasp the correspondence between each of the plurality of devices on the X-ray image and each of the plurality of devices of the remote catheter system by the processing circuitry illustrated in FIG. 3.

FIG. 4 is a flowchart illustrating an example of a procedure when processing for allowing the user to easily grasp the correspondence between each of the plurality of devices on the X-ray image and each of the plurality of devices 22 of the remote catheter system by the processing circuitry 44 illustrated in FIG. 3. In FIG. 4, reference numerals with S indicate steps of the flowchart.

Figure 5:
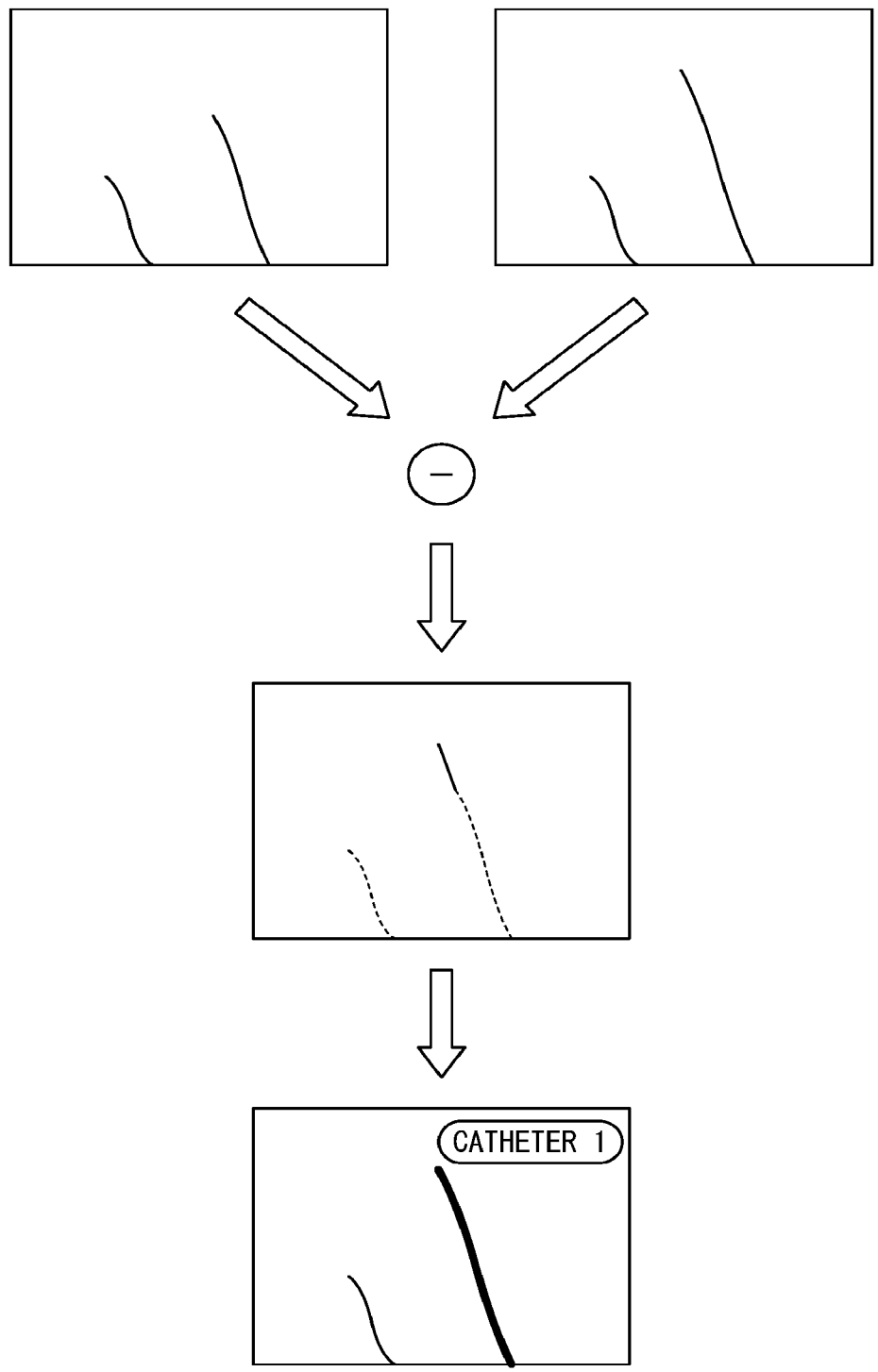
FIG. 5 is an explanatory view illustrating an example of a state where the entire device to be operated on the X-ray image is identified and displayed by the procedure illustrated in FIG. 4.

Moreover, FIG. 5 is an explanatory view illustrating an example of a state where the entire device to be operated on the X-ray image is identified and displayed by the procedure illustrated in FIG. 4.

FIGS. 4 and 5 include images of the two devices on the X-ray image and illustrate an example of a case where either one of them is the device to be operated during the operation by the user and another is the stationary device.

First, the X-ray image obtaining function 51 obtains a medical image obtained by imaging the object O. The X-ray image obtaining function 51 sequentially obtains (Step S1) the X-ray images continuously in a time series generated on the basis of projection data obtained by X-ray imaging of the object O continuously in a time series.

Subsequently, at Step S2, the specifying function 52 subtracts a second X-ray image imaged a predetermined time prior to a first X-ray image from the first X-ray image. For example, the specifying function 52 only needs to handle the latest X-ray image as the first X-ray image and the X-ray image imaged the predetermined time prior to the first X-ray image as the second X-ray image each time the X-ray images continuously in a time series are sequentially obtained.

Subsequently, the specifying function 52 specifies the device to be operated on the basis of movement of the device in the medical image when the device 22 is operated by the remote input circuit 33. For example, the specifying function 52 extracts the device which has moved during the predetermined time in the plurality of devices included in the first X-ray image (Step S3). This extracted device is a device which has moved during the predetermined time since the user carried out the operation, that is, the device to be operated by the user (active device). On the other hand, the device not extracted, that is, the stationary device is a device not to be operated by the user (non-active device). The specifying function 52 specifies the extracted device in the devices in the medical image as the active device and stores it in the memory circuitry 43 and specifies the device not extracted as the non-active device and stores it in the memory circuitry 43 (Step S4).

A method of identifying the device to be operated and the device not to be operated will be described more specifically. The processing circuitry 44 identifies to which of the devices 22 each of the images of the plurality of devices on the X-ray image corresponds in advance. The processing circuitry 44 stores information indicating each of the images of the plurality of devices on the X-ray image and information on an ID defined for each of the plurality of devices 22, for example (a "catheter 1" and a "catheter 2", for example) in association in the memory circuitry 43. With this associated information, the specifying function 52 further associates information that the device extracted at Step S3 is the active device and information that the device other than the extracted device is the non-active device at Step S4.

Subsequently, at Step S5, the identifying function 53 generates an image in which the device 22 to be operated can be identifiable by the remote input circuit 33 on the basis of a specification result of the specifying function 52. Specifically, the identifying function 53 generates an image identifiably displaying the entire device to be operated which is specified by the specifying function 52 on the first X-ray image. Then, the identifying function 53 superimposes the image identifiably displaying the entire device to be operated on the first X-ray image and displays it on the display 18 or the display of the display input circuit 31 (hereinafter referred to as identification display of the device to be operated).

As a mode of identification display, various modes which can identify the device to be operated can be used such as coloring the entire device to be operated, superimposing or fringing with a bold line, increasing brightness, flashing, displaying character information indicating that the device is to be operated or combinations of them (see the lowest stage in FIG. 5, for example). Moreover, it may be a mode in which the identification display is periodically flashed by periodically switching between the identification display and normal display (cancellation of the identification display).

If the display 23 is provided on the support member of the robot arm 21, the identifying function 53 presents at least the information which can identify the device to be operated in the plurality of devices 22 to the user through the display 23. The display 23 may be an indicator constituted by a plurality of LEDs, for example.

Subsequently, at Step S6, the switching function 54 determines whether the identification display is to be turned OFF or not. If the identification display is to be turned OFF, a series of procedures is finished. On the other hand, if the identification display is ON, a routine returns to Step S1 and obtains a new X-ray image.

The switching function 54 has a function of automatically switching between turning ON/OFF of the identification display of the device to be operated. Specifically, the switching function 54 turns ON the identification display if a predetermined superimposing condition is satisfied, while it turns OFF the identification display, if a predetermined erasing condition is satisfied.

A predetermined superimposing condition includes a change of an imaging position, start of imaging, user instruction (including voice recognition) that the identification display should be made through the input circuit 42 and the like. A change of a distal end position of the device only by a predetermined distance may be used as the predetermined superimposing condition. If the device is a so-called active catheter with an angle of a distal end portion thereof constituted variable, the switching function 54 determines that the predetermined superimposing condition is satisfied when the angle of the distal end portion of the device included in the first X-ray image is changed, and the identification display may be turned ON.

A predetermined erasing condition includes elapsing of certain time from turning-ON of the identification display, the user instruction (including the voice recognition) that the identification display should be finished through the input circuit 42 and the like.

By means of the aforementioned procedures, the user can easily grasp the correspondence between each of the plurality of devices on the X-ray image and each of the plurality of devices 22 of the remote catheter system.

When Step S3 is executed, as illustrated in a middle stage in FIG. 5, the specifying function 52 specifies only a portion which has moved during the predetermined time in the image of the device to be operated. However, a size of the portion which has moved might be small in many cases. Thus, even if the portion specified by executing Step S3 is presented to the user, it is difficult for the user to find this specified portion on the first X-ray image. Moreover, it is also difficult to identify which of end points of this specified portion is a distal end.

With this regard, since the entire device to be operated is identified and displayed according to the aforementioned procedures, if images of the plurality of devices are included in the X-ray mage, the user can easily grasp the correspondence between each of the plurality of devices on the X-ray image and each of the plurality of devices 22 of the remote catheter system. Thus, the user can instinctively grasp which device to be operated the user is operating only by checking the X-ray image. Therefore, the user is freed from a burden of memorizing a position of the device to be operated and a burden of visually following it and can concentrate on manipulation. Moreover, a misoperation caused by misrecognition of the device to be operated can be prevented. If the identification display is not needed, the identification display can be turned OFF, and the identification display does not interfere with manipulation of the user.

FIG. 4 illustrates an example of a case when the X-ray image obtaining function 51 sequentially obtains the X-ray images on a real time basis, but the procedure in FIG. 4 may be executed as a post process to a plurality of the X-ray images obtained beforehand.

Figure 6A:
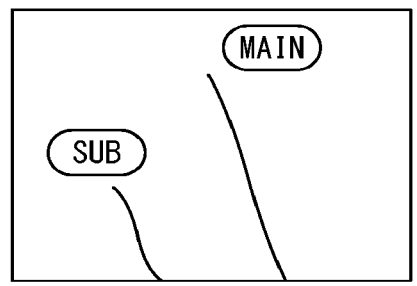
FIG. 6A is an explanatory view of a first variation of the identification display.
Figure 6B:
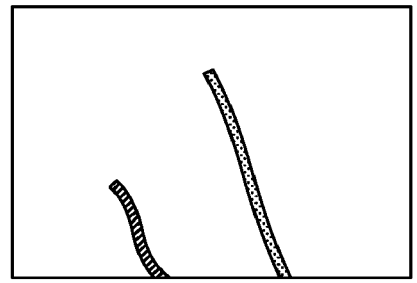
FIG. 6B is an explanatory view of a second variation of the identification display.
Figure 6C:
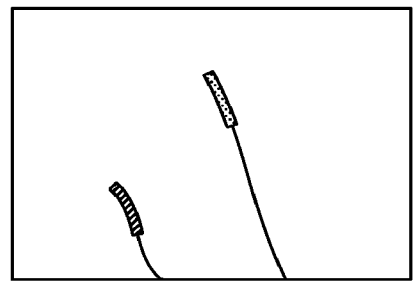
FIG. 6C is an explanatory view of a third variation of the identification display.

FIG. 6A is an explanatory view of a first variation of the identification display, FIG. 6B for a second variation, and FIG. 6C for a third variation, respectively. As illustrated in FIG. 6, the identification display may be conducted not only for the device to be operated but also for the device not to be operated. For example, as illustrated in FIG. 6A, the display 18 and the display of the display input circuit 31 may display information indicating a role of each device or as illustrated in FIG. 6B, entireties of the devices may be colored by colors different from each other and determined in advance. As illustrated in FIG. 6C, the display 18 and the display of the display input circuit 31 may conduct the identification display so that a part of each device is colored. FIG. 6C illustrates an example of a case when only a predetermined length from a distal end of each device is subjected to the identification display.

Figure 7:
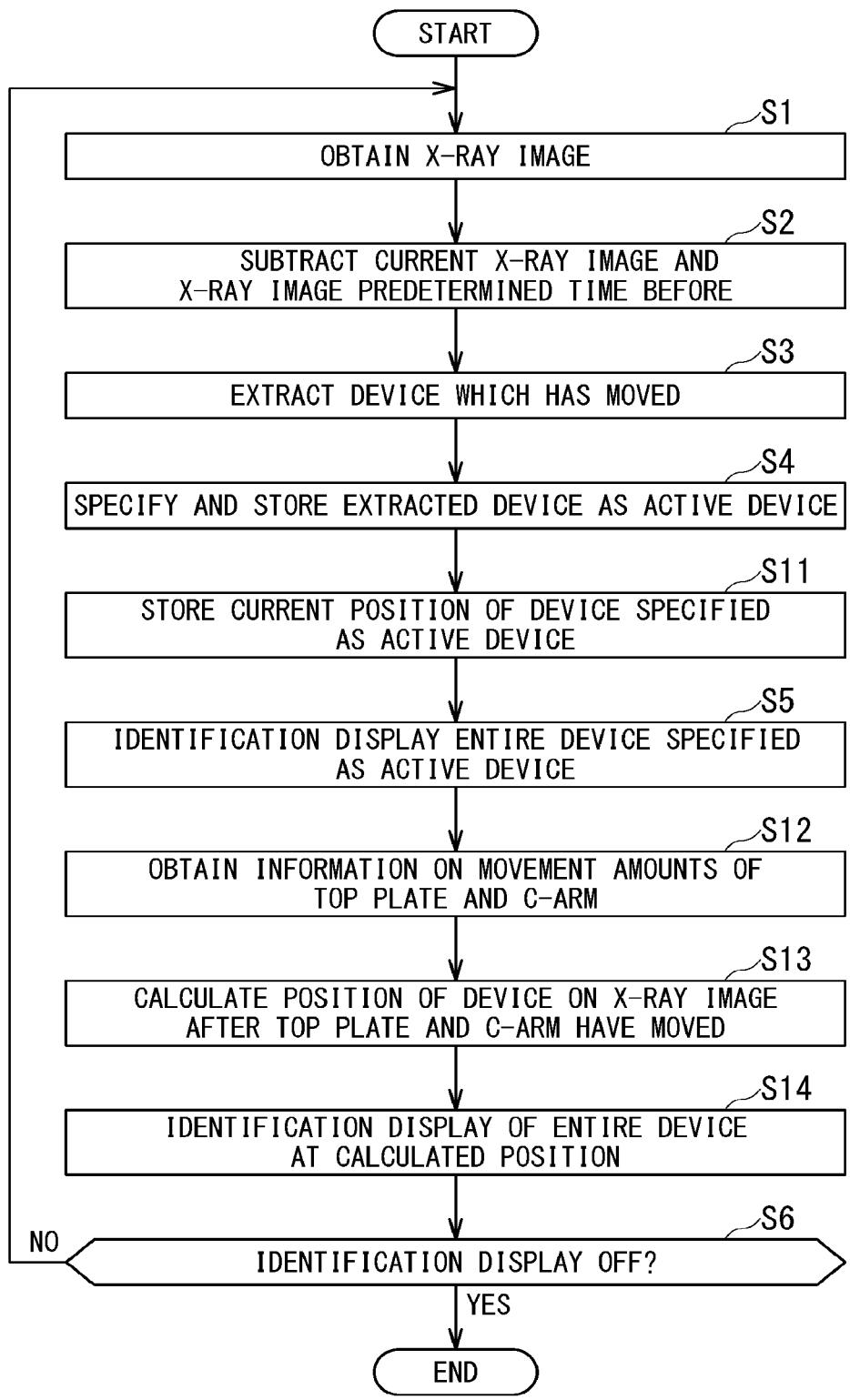
FIG. 7 is a flowchart illustrating an example of a procedure for causing the identification display to be followed if the C-arm or the top plate of the bed is further moved in addition to the procedures illustrated in FIG. 4.

FIG. 7 is a flowchart illustrating an example of a procedure for causing the identification display to be followed if the C-arm 15 or the top plate 17 of the bed 16 is further moved in addition to the procedures illustrated in FIG. 4. Same reference numerals are given to equivalent steps in FIG. 4 and duplicated explanation will be omitted.

Figure 8:
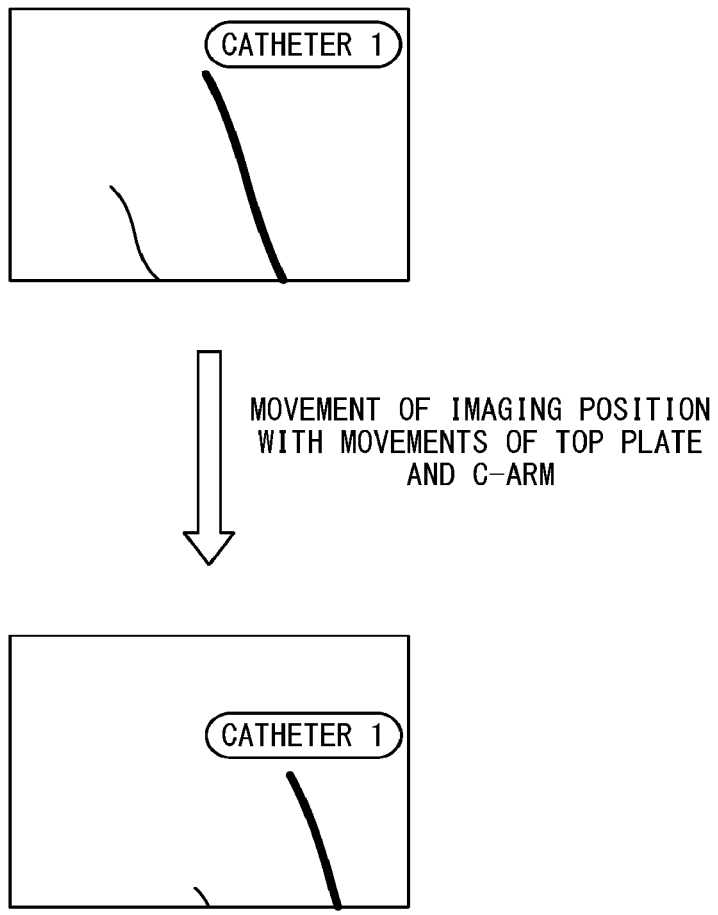
FIG. 8 is an explanatory view illustrating an example of a state where the identification display is followed when the C-arm or the top plate of the bed 16 is moved by the procedures illustrated in FIG. 7.

FIG. 8 is an explanatory view illustrating an example of a state where the identification display is followed when the C-arm 15 or the top plate 17 of the bed 16 is moved by the procedures illustrated in FIG. 7.

At Step S11, the following function 55 stores a current position of the device to be operated which is specified by the specifying function 52 on the X-ray image in the memory circuitry 43.

At Step S12, the bed movement-amount obtaining function 56 obtains a movement amount of the top plate 17 of the bed 16 on which the object O is placed. The C-arm movement-amount obtaining function 57 obtains a movement amount of an X-ray irradiation shaft of an imaging system which carries out X-ray imaging by obtaining the movement amount of the C-arm 15. The movement amount of the top plate 17 of the bed 16 and the movement amount of the C-arm 15 are constituted by amounts of parallel movement along orthogonal three axes (three-dimensional vectors, for example) and rotational movement around the orthogonal three axes.

Subsequently, at Step S13, the following function 55 acquires a position of the device to be operated on the X-ray image after movement of the top plate 17 of the bed 16 and the C-arm 15 on the basis of the movement amount of the top plate 17 of the bed 16 and the movement amount of the C-arm 15. At this time, the following function 55 may correct the movement amount on the basis of a height of the bed 16 or an enlargement rate on the display of the X-ray image.

Subsequently, at Step S14, the identifying function 53 conducts identification display of the entirety of the device to be operated at the position after the movement (see FIG. 8).

Here, processing at Step S11 and Step S13 will be described more specifically. If the top plate 17 of the bed 16 and the C-arm 15 are moved in parallel, for example, the following function 55 only needs to acquire a coordinate of the device to be operated after the movement on the X-ray image on the basis of the information on the parallel movement amount.

On the other hand, if it is assumed that movements of the top plate 17 of the bed 16 and the C-arm 15 include rotational movement, at Step S11, the 3D-image obtaining function 58 obtains a three-dimensional medical image data of the object O. As this three-dimensional medical image data, volume data of a CT image and an MRI image of the object O obtained by an X-ray CT (computed tomography) device and an MRI (Magnetic Resonance Imaging) device and the like in advance can be used. In this case, at Step S11, the following function 55 specifies a position in a blood vessel into which the device to be operated which is specified by the specifying function 52 is inserted and specifies a three-dimensional coordinate of this device on the X-ray image for each of the blood vessel on the three-dimensional medical image and a blood-vessel shape of the first X-ray image. Then, at Step S13, the following function 55 only needs to acquire a positional coordinate of the device to be operated after the movements of the top plate 17 of the bed 16 and the C-arm 15 on the X-ray image on the basis of the information on the rotational movement amount of the top plate 17 of the bed 16.

By means of the aforementioned procedures, even if a visual field of the X-ray image is moved after the C-arm 15 and the top plate 17 of the bed 16 have been moved, the identification display can be made to follow.

If the procedure is executed each time the X-ray images are sequentially obtained on the real time basis, the identification display can be made to follow on the real time basis. Even if X-ray irradiation is not carried out during movement of the C-arm 15 or the top plate 17 of the bed 16, the identification display can be made to follow by applying the procedure illustrated in FIG. 7 to the X-ray image imaged before and after the movement.

The procedures illustrated in FIG. 7 exert an effect similar to that by the procedure illustrated in FIG. 4. According to the procedures illustrated in FIG. 7, even if the C-arm 15 or the top plate 17 of the bed 16 has been moved, the entire device to be operated is identified and displayed on the X-ray image and thus, the user can further concentrate on the manipulation.

Figure 9:
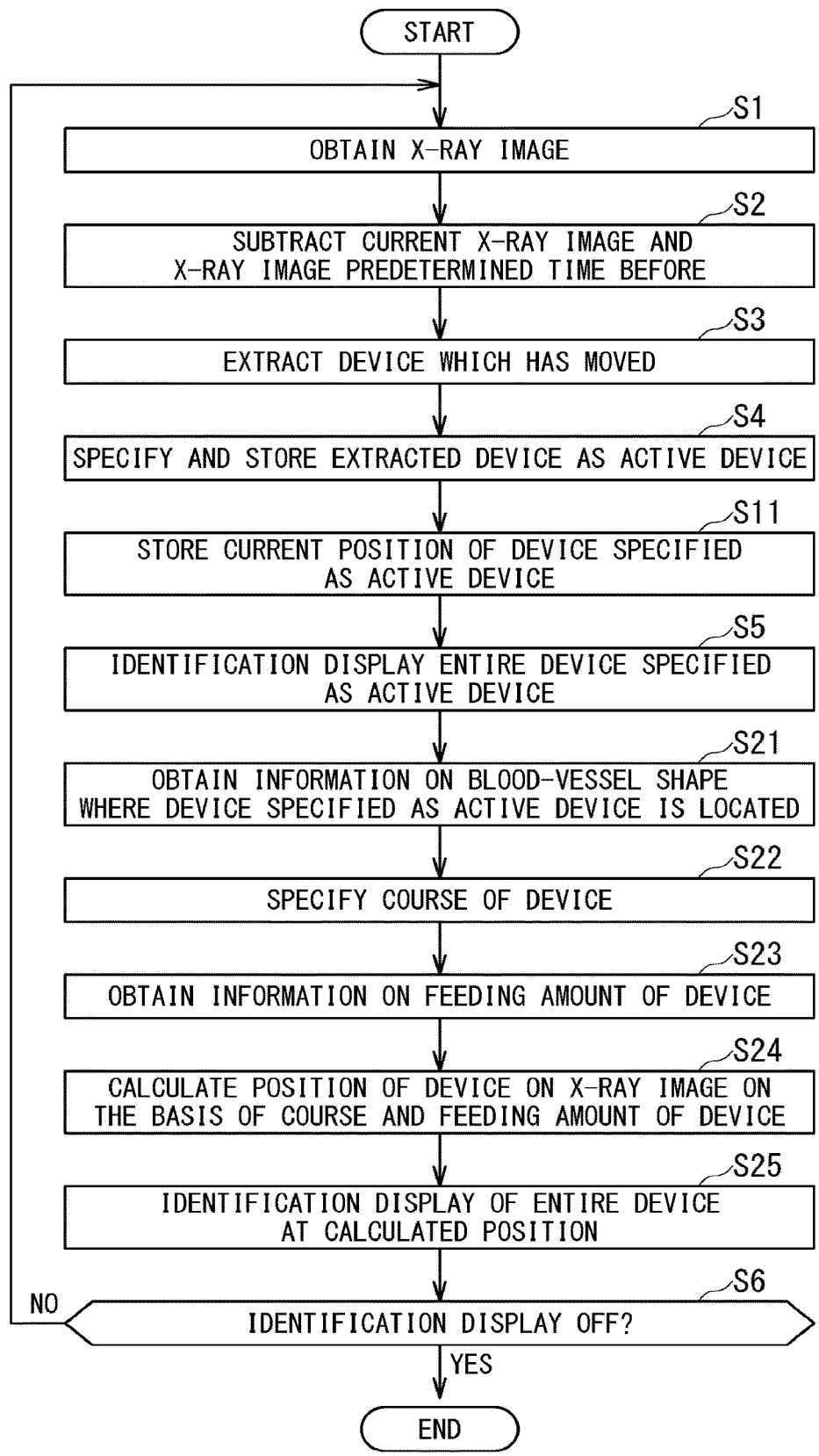
FIG. 9 is a flowchart illustrating an example of a procedure when the identification display is made to follow further on the basis of a feeding amount of the device in addition to the procedure illustrated in FIG. 4.

FIG. 9 is a flowchart illustrating an example of a procedure when the identification display is made to follow further on the basis of a feeding amount of the device in addition to the procedure illustrated in FIG. 4. The same reference numerals are given to equivalent steps in FIGS. 4 and 7 and duplicated explanation will be omitted.

Figure 10:
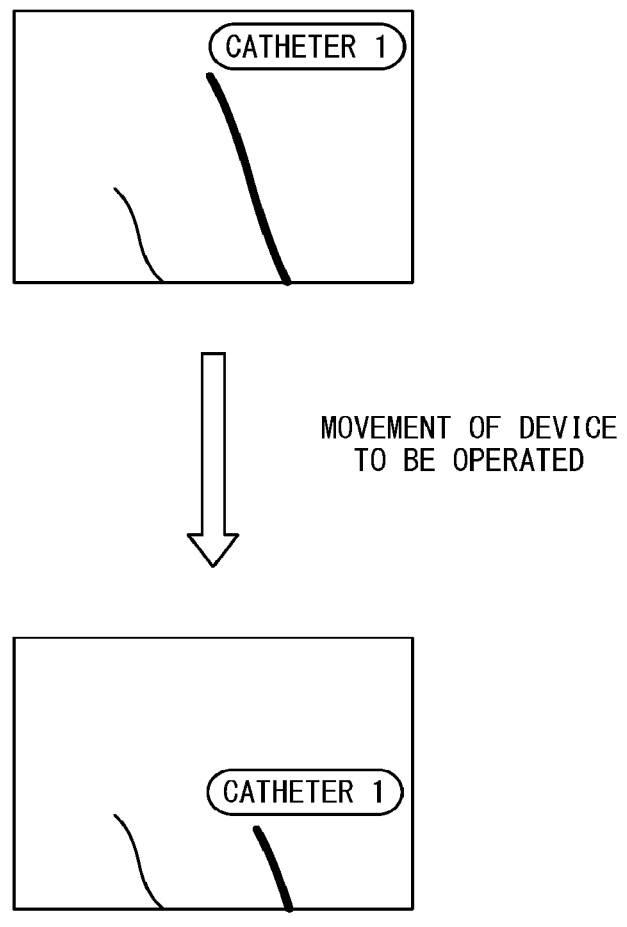
FIG. 10 is an explanatory view illustrating an example of a state where the identification display is made to follow on the basis of the feeding amount of the device by the procedure illustrated in FIG. 9.

FIG. 10 is an explanatory view illustrating an example of a state where the identification display is made to follow on the basis of the feeding amount of the device by the procedure illustrated in FIG. 9.

At Step S11, the 3D-image obtaining function 58 obtains the three-dimensional medical image data of the object O. The following function 55 specifies a position in the blood vessel into which the device to be operated which is specified by the specifying function 52 is inserted and specifies the three-dimensional coordinate of this device on the X-ray image for each of the blood vessel on the three-dimensional medical image and the blood-vessel shape of the first X-ray image.

At Step S21, the following function 55 obtains information on the blood-vessel shape where the device to be operated is located on the basis of the three-dimensional medical image.

Subsequently, at Step S22, the following function 55 specifies a course of the device to be operated on the basis of the information on the blood-vessel shape where the device to be operated is located and traveling of the contrast agent on the X-ray image.

Subsequently, at Step S23, the feeding-amount obtaining function 59 obtains information on the feeding movement amount of the device to be operated from the processing circuitry of the control device 34 of the remote console 30.

Subsequently, at Step S24, the following function 55 acquires the position on the first X-ray image after feeding movement on the basis of the specified course of the device to be operated and the information on the feeding movement amount. At this time, the following function 55 may correct the movement amount on the basis of the height of the bed 16 and the enlargement rate on the display of the X-ray image.

Subsequently, at Step S25, the identifying function 53 identifies and displays the entire device to be operated at the position after the movement (see FIG. 10).

By means of the aforementioned procedures, the identification display can be made to follow on the basis of the feeding amount of the device. The procedures illustrated in FIG. 9 exert an effect similar to that by the procedure illustrated in FIG. 4. According to the procedures illustrated in FIG. 9, even if the device to be operated has been moved, the entire device to be operated is identified and displayed on the X-ray image by being followed and thus, the user can further concentrate on the manipulation. Moreover, the procedure illustrated in FIG. 9 can be executed at the same time and in parallel in combination with the procedures illustrated in FIG. 7.

In FIGS. 4, 7, and 9, an example of a case where images of two devices are included on the X-ray image, one of which is a moving device and another is a stationary device is illustrated as described above, but the both two devices included in the X-ray image may be moving devices.

For example, the remote input circuit 33 may be constituted capable of operating the two devices 22 at the same time. Moreover, two remote input circuits 33, that is, a first remote input circuit 33 and a second remote input circuit 33 corresponding to each of the two devices 22 may be provided. In this case, the two devices 22 might be operated at the same time.

In this case, if the two devices 22 are operated at the same time in the procedures illustrated in FIG. 9, for example, the following function 55 only needs to predict the position of each device 22 on the X-ray image on the basis of the feeding movement amount of each of the devices 22 and to identify and to display the entirety of each of the devices 22 at the predicted positions after the movement.

Moreover, the specifying function 52 only needs to associate each of the two devices moving at the same time on the X-ray image and each of the plurality of devices 22 with each other on the basis of the feeding amounts of the devices, for example.

Figure 11:
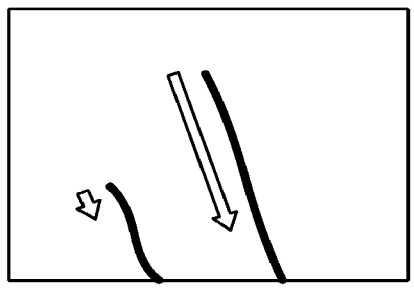
FIG. 11 is an explanatory view illustrating an example of a state where a correspondence between each of the two devices on the X-ray image and each of the plurality of the actual devices is specified by using the feeding movement amounts of the devices.
Figure 11:
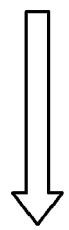
Figure 11:
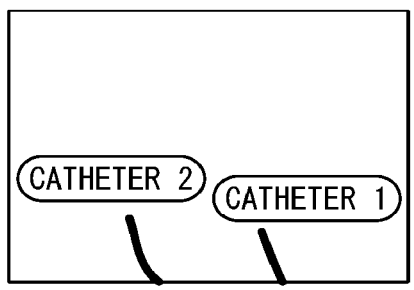

FIG. 11 is an explanatory view illustrating an example of a state where a correspondence between each of the two devices on the X-ray image and each of the plurality of the actual devices 22 is specified by using the feeding movement amounts of the devices. For example, the following function 55 predicts a position on the X-ray image after the feeding movement on the basis of the course of each of the devices 22 and the information on the feeding movement amount by a method similar to the method described by using FIG. 9. Then, the specifying function 52 can specify the correspondence between each of the two devices on the X-ray image and each of the plurality of the actual devices 22 by comparing this predicted position on the basis of the feeding movement amount with the movement amount of the image of each of the devices 22 having actually moved on the X-ray image (FIG. 11).

Second Embodiment

Subsequently, a second embodiment of the X-ray diagnosis apparatus and a medical image diagnosis system according to the present invention will be described.

Figure 12:
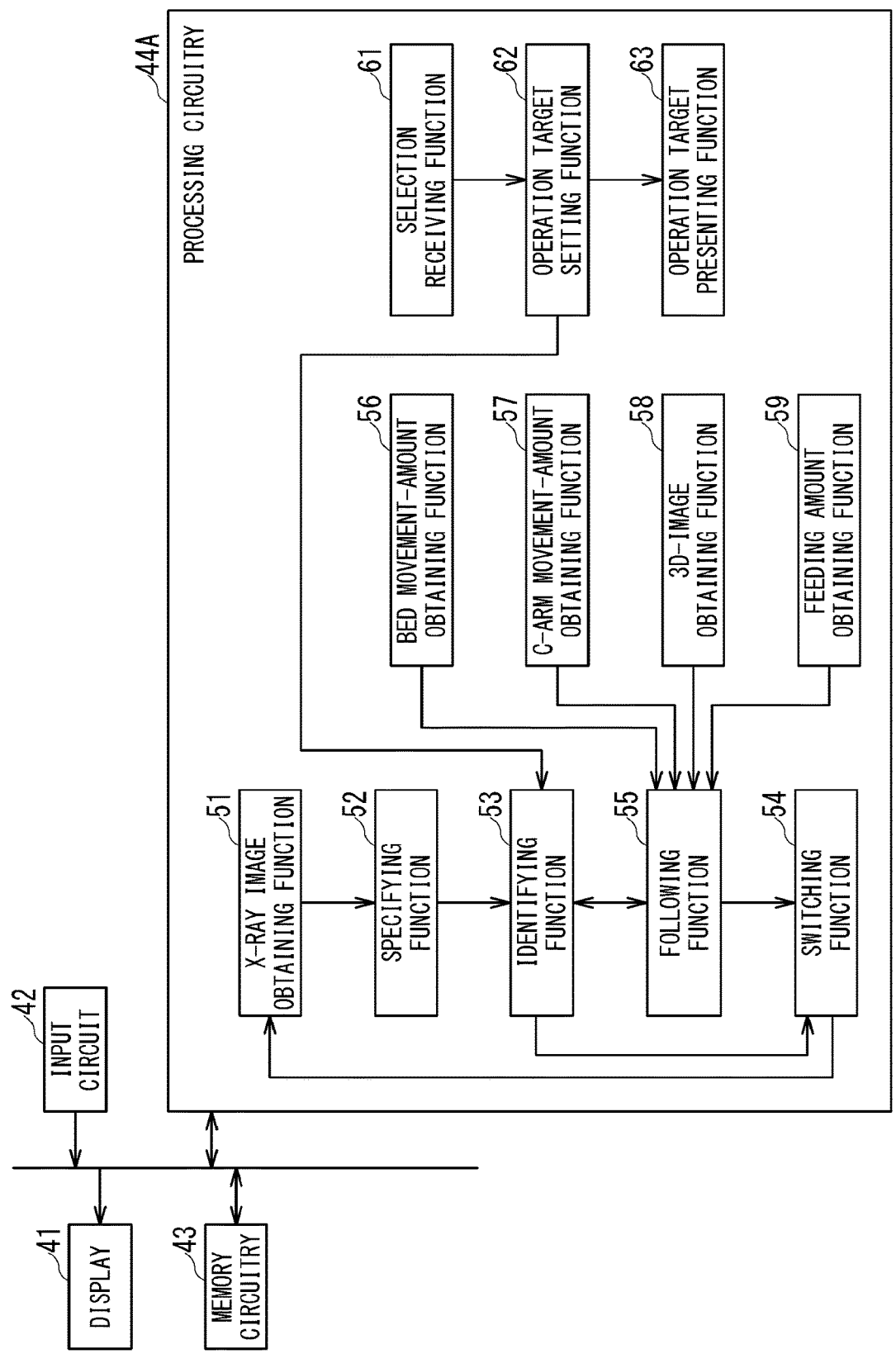
FIG. 12 is a block diagram illustrating a constitution example of the image processing device according to the second embodiment.

FIG. 12 is a block diagram illustrating a constitution example of the image processing device 12 according to the second embodiment.

Processing circuitry 44A of the image processing device 12 illustrated in this second embodiment has a function of setting a device to be operated in accordance with device selection information of the user through the remote console 30 added as compared with the processing circuitry 44 illustrated in the first embodiment. Since other constitutions and actions are substantially similar to the processing circuitry 44 illustrated in FIG. 3, same reference numerals are given to same constitutions and explanation will be omitted.

As illustrated in FIG. 12, the processing circuitry 44A further realizes a selection receiving function 61, an operation target setting function 62, and an operation target presenting function 63 in addition to each of the functions 51 to 59. Each of these functions is stored in the memory circuitry 43 in a form of a program, respectively. Details of an operation of each of the functions will be described below by referring to FIGS. 13 and 14.

Similarly to the processing circuitry 44 according to the first embodiment, the processing circuitry 44A identifies to which of the devices 22 each of images of a plurality of devices on the X-ray image corresponds in advance. The processing circuitry 44A stores information indicating each of the images of the plurality of devices on the X-ray image and information on ID defined for each of the plurality of devices 22, for example (a "catheter 1" and a "catheter 2", for example) in association in the memory circuitry 43.

Figure 13:
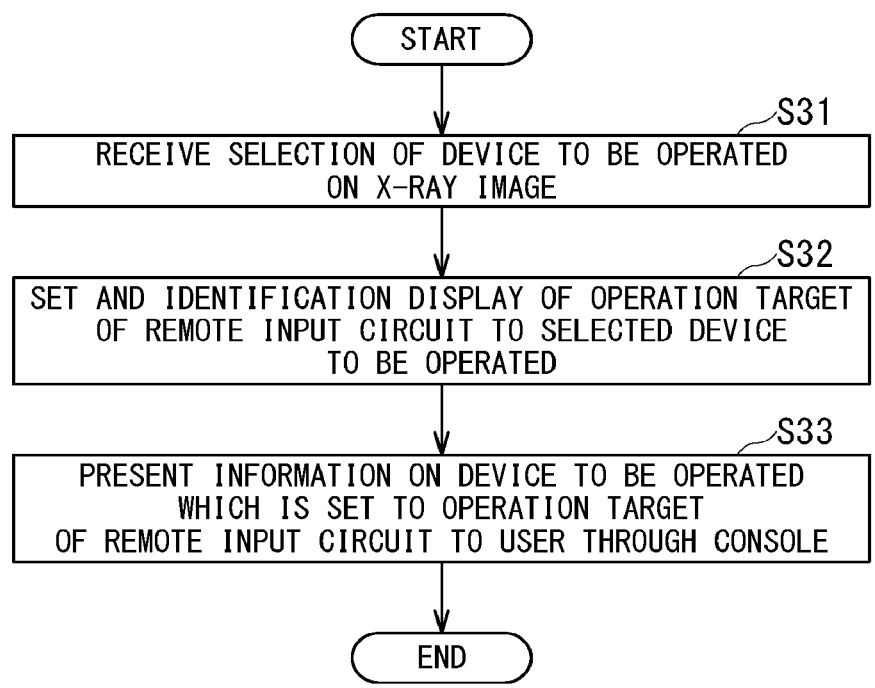
FIG. 13 is a flowchart illustrating an example of a procedure when a device to be operated is to be set by the processing circuitry illustrated in FIG. 12 in accordance with device selection information of the user through the remote console.
Figure 14:
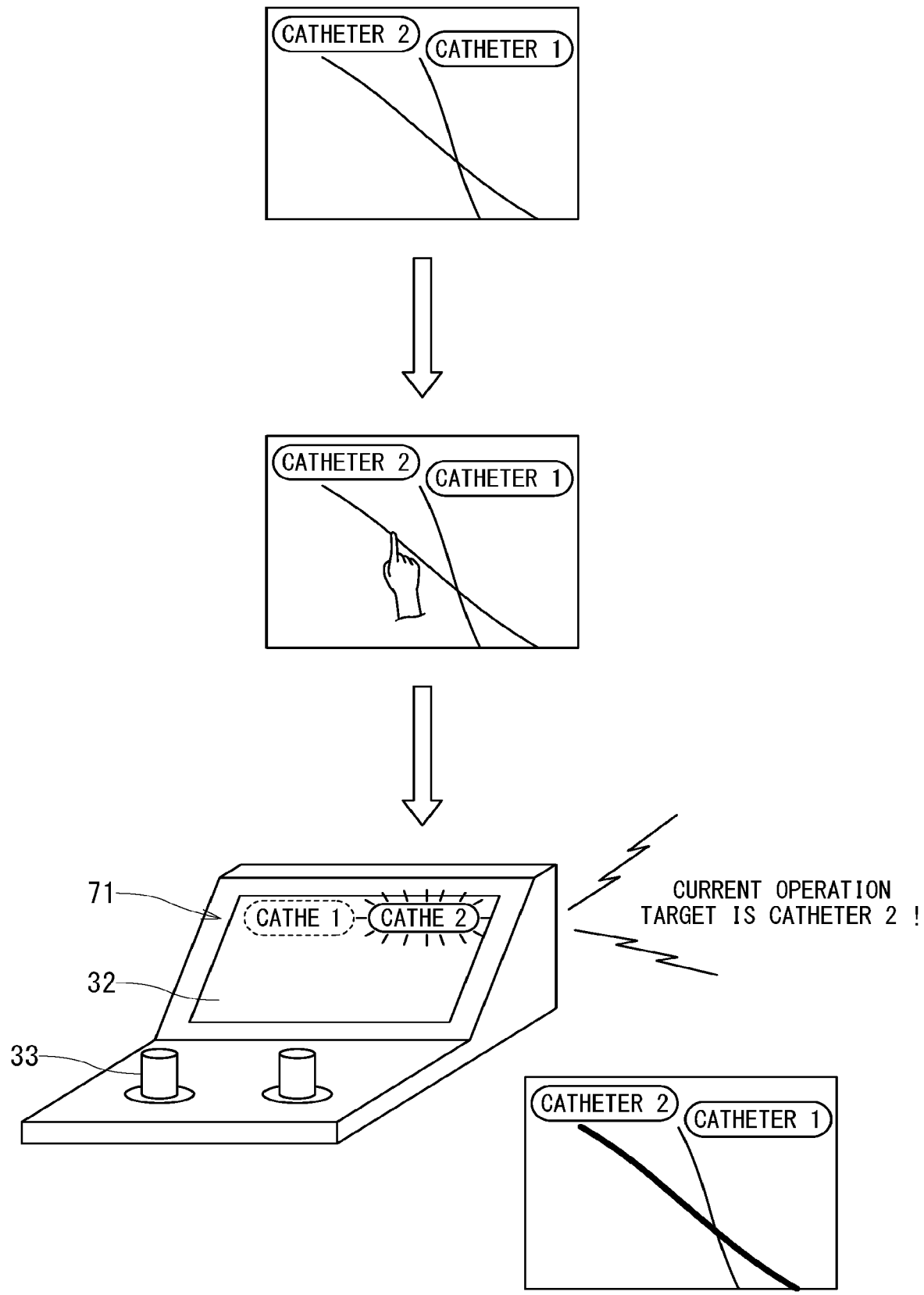
FIG. 14 is an explanatory view illustrating an example of a state where the device to be operated is to be set in accordance with the device selection information of the user through the remote console by the procedure illustrated in FIG. 13.

FIG. 13 is a flowchart illustrating an example of a procedure when a device to be operated is to be set by the processing circuitry 44A illustrated in FIG. 12 in accordance with device selection information of the user through the remote console 30. This procedure can be executed at the same time and in parallel with the procedures illustrated in FIGS. 4, 7, and 9. FIG. 14 is an explanatory view illustrating an example of a state where the device to be operated is to be set in accordance with the device selection information of the user through the remote console 30 by the procedure illustrated in FIG. 13.

At Step S31, the selection receiving function 61 receives selection of the user to the device included in the first X-ray image. For example, the user instructs the device the user desires to operate to the processing circuitry of the control device 34 through a touch panel of the display input circuit 31 or 32, a hard key or the like of the remote input circuit 33 (see medium stage in FIG. 14). The processing circuitry of the control device 34 gives this instruction information to the selection receiving function 61. The user can switch the active device, for example, by this selection instruction.

If the selection instruction is to be received through the hard key of the remote input circuit 33, the selection receiving function 61 may sequentially switch the device 22 to be operated cyclically each time the hard key is pressed down, for example. At this time, an order of cyclic switching is preferably an order of the number of times of use in the past.

Subsequently, at Step S32, the operation target setting function 62 sets the device selected by the user to a device to be operated of the remote input circuit 33 by assigning an operation authority of the remote input circuit 33 to the device selected by the user. For example, if the remote input circuit 33 is constituted capable of selective operation of either one of the two devices 22, the device 22 selected by the user is set to the device to be operated of the remote input circuit 33, while another device 22 is set incapable of being operated by the remote input circuit 33. Moreover, if the remote input circuit 33 corresponding to each of the two devices 22 is provided, an operation by the remote input circuit 33 corresponding to the device not to be operated may be prohibited.

Subsequently, at Step S33, the operation target presenting function 63 presents information on the current device to be operated of the remote input circuit 33 to the user of the remote input circuit 33 in collaboration with the processing circuitry of the control device 34.

Methods of this presentation include a method of displaying an image 65 illustrating the device to be operated on the display of the display input circuit 32, a method of guiding the device to be operated by voice through a speaker, not shown, of the remote console 30 and the like, for example (see lower left stage in FIG. 14). The image 65 can be any image as long as it can be identified by the current device to be operated after the selection instruction and may be a symbol or an arrow, for example. The image 65 may include information playing a role of each device (information indicating whether the device is a main catheter or a sub catheter, for example).

It is needless to say that the device to be operated on the X-ray image displayed on the display of the display input circuit 31 or 32 may be identified and displayed (see lower right stage in FIG. 14). As a mode of the identification display, various modes which can identify the selected device to be operated can be used such as coloring at least a part of the selected device to be operated, superimposing of fringing with a bold line, increasing brightness, flashing, displaying character information indicating that the device is to be operated or combinations of them. The information on the current device to be operated of the remote input circuit 33 may be presented on the display 18 of the X-ray diagnosis apparatus 11. Alternatively, the information on the current device to be operated after the selection instruction may be presented on the display 23 provided on the support member constituting the robot arm 21.

The "voice" refers to sound made by reading text data by sound recognized as a human voice by a listener. The "sound" is assumed to include not only the "voice" but also "music" or "effect sound" (beep sound and the like)".

By means of the aforementioned procedures, the device to be operated can be set in accordance with the device selection information of the user through the remote console 30.

There are cases where it is difficult for the user to grasp the correspondence between each of the two devices on the X-ray image and each of the actual two devices 22 such as a case where the two devices included in the first X-ray image are close to each other and the like. In this case, the processing circuitry 44A only needs to move one of the devices only slightly and automatically to a returning direction of the device, for example. By means of movement of one of the devices, the user can grasp the intended device more easily. This automatic movement processing only needs to be executed by the processing circuitry 44A if there is an input before Step S31 that the selection instruction is to be made by the user or that the two devices are close to each other on the image, for example.

According to the medical image diagnosis system 10 according to the second embodiment, an effect similar to that of the medical image diagnosis system 10 according to the first embodiment is exerted, and the user can switch the device to be operated easily and can easily grasp the current device to be operated after the switching.

Third Embodiment

Subsequently, a third embodiment of an X-ray diagnosis apparatus and a medical image diagnosis system according to the present invention will be described.

The medical image diagnosis system 10 illustrated in the third embodiment is different from the first embodiment in points that the device not to be operated of the plurality of devices 22 of the remote catheter system can take a plurality of states and an optical camera 70 for imaging at least either one of the object O and an operator is provided. Since other constitutions and actions are substantially same as those of the medical image diagnosis system 10 illustrated in FIG. 1, same reference numerals are given to the same constitutions and explanation will be omitted.

In the third embodiment, the device not to be operated has one of or a combination of four states, that is, a free state, a weakly fixed state, a strongly fixed state, and a pressure-applied state.

Here, the term "free" refers to a state where no force is applied to the device not to be operated. Terms "weakly fixed" and "strongly fixed" refer to a state where the device not to be operated is to keep the current state. The "weakly fixed" is assumed to be a state where a force repelling an external force within a predetermined range is applied to the device not to be operated so that the device not to be operated would not move even if the external force is applied. On the other hand, the "strongly fixed" is assumed to be a state where a force repelling the external force within the predetermined range or more is applied to the device not to be operated so that the device not to be operated would not move even if the external force is applied.

The term "pressure-applied" refers to a state where the device not to be operated is hooked by a predetermined target is to be kept. The "pressure-applied" state of the device not to be operated is used when another device to be operated is to be held so that it does not protrude to an outer side of an aneurysm. In the "pressure-applied", its direction of a force applied to the device not to be operated and intensity need to be controlled so that the hooked state with respect to the predetermined target should be maintained.

The user instructs setting of a state of the device not to be operated to the processing circuitry of the control device 34 through the touch panel of the display input circuit 31 or 32 or the hard key of the remote input circuit 33 and the like. The processing circuitry of the control device 34 controls a state of the device not to be operated in accordance with this setting instruction.

Figure 15:
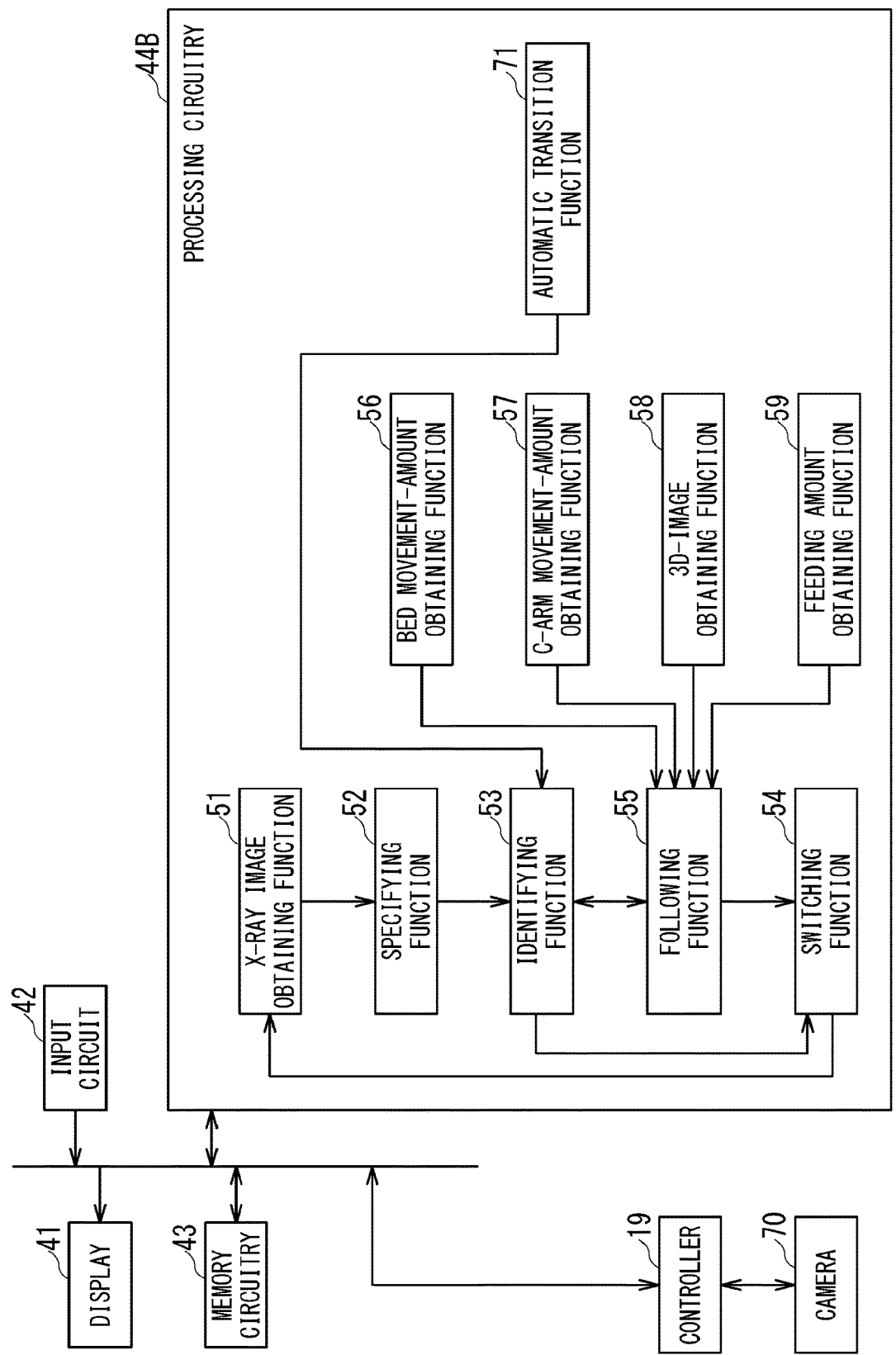
FIG. 15 is a block diagram illustrating a constitution example of the image processing device according to the third embodiment.

FIG. 15 is a block diagram illustrating a constitution example of the image processing device 12 according to the third embodiment. The camera 70 does not have to be included in the X-ray diagnosis apparatus 11.

The camera 70 captures at least either one of an image capable of detecting movement of the object O and an image capable of detecting a visual line of the operator. When the visual line of the operator is to be imaged, an image pickup element included in a glasses-type device attached on a head part of the object O may be used as the camera 70.

Processing circuitry 44B realizes an automatic transition function 71 further in addition to each of the functions 51 to 59. Each of these functions is stored in the memory circuitry 43 in a form of a program.

Similarly to the processing circuitry 44 according to the first embodiment, the processing circuitry 44B identifies to which of the devices 22 each of images of the plurality of devices on the X-ray image corresponds in advance. The processing circuitry 44B stores information indicating each of the images of the plurality of devices on the X-ray image and information on an ID defined for each of the plurality of devices 22, for example (a "catheter 1" and a "catheter 2", for example) in association in the memory circuitry 43.

The automatic transition function 71 causes a state of the device not to be operated to automatically change between the weakly fixed state and the strongly fixed state on the basis of the image imaged by the camera 70.

For example, if an image imaged by the camera 70 is an image capable of detecting movement of the object O, the automatic transition function 71 only needs to set the weak fixation when the movement of the object O is at a predetermined degree or more and to set the strong fixation when the movement is at the predetermined degree or less. If an image imaged by the camera 70 is an image capable of detecting the visual line of the operator, the automatic transition function 71 only needs to set the weak fixation when the visual line of the operator is far away and to set the strong fixation when the visual line is not far away.

Similarly to the method of presentation of information on the current device to be operated according to the second embodiment, the automatic transition function 71 may present information that the state of the device not to be operated of the remote input circuit 33 is subjected to automatic transition to the user of the remote input circuit 33 in collaboration with the processing circuitry of the control device 34.

The medical image diagnosis system 10 according to the third embodiment exerts an effect similar to that of the medical image diagnosis system 10 according to the first embodiment and is capable of automatic transition of the state of the device not to be operated between the weakly fixed state and the strongly fixed state on the basis of at least either one of the movement of the object O and the visual line of the operator. Moreover, the processing circuitry 44B according to the third embodiment may realize the functions 61 to 63 according to the second embodiment.

Fourth Embodiment

Subsequently, a fourth embodiment of an X-ray diagnosis apparatus and a medical image diagnosis system according to the present invention will be described.

Figure 16:
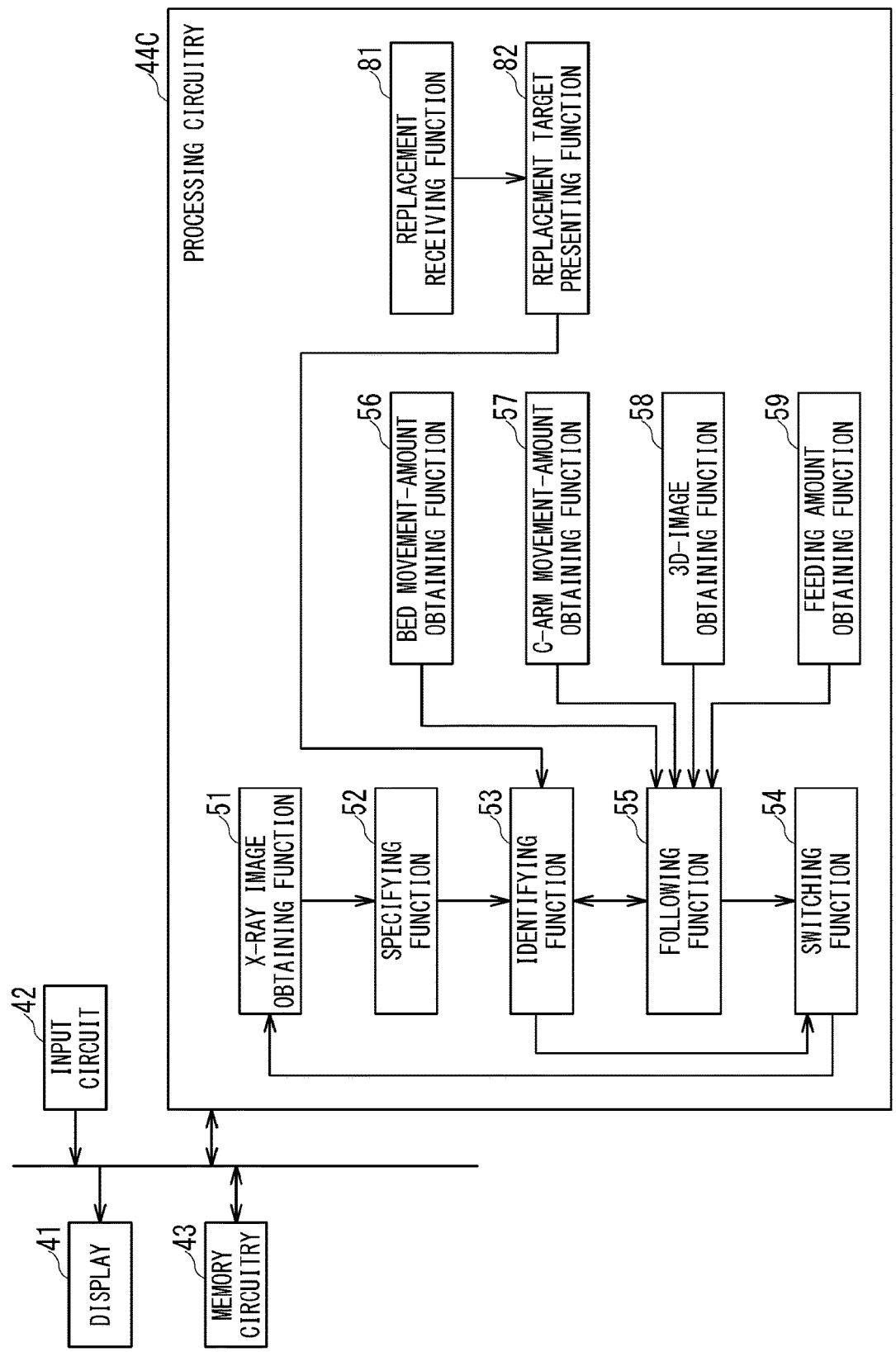
FIG. 16 is a block diagram illustrating a constitution example of the image processing device according to the fourth embodiment.

FIG. 16 is a block diagram illustrating a constitution example of the image processing device 12 according to the fourth embodiment.

Processing circuitry 44C of the image processing device 12 illustrated in this fourth embodiment has a function of setting a device to be replaced in accordance with device selection information on a replacement target of the user added to the processing circuitry 44 illustrated in the first embodiment. Since other constitutions and actions are substantially same as those of the processing circuitry 44 illustrated in FIG. 3, same reference numerals are given to same constitutions and explanation will be omitted.

As illustrated in FIG. 16, the processing circuitry 44C further realizes a replacement receiving function 81 and a replacement target presenting function 82 in addition to each of the functions 51 to 59. Each of these functions is stored in the memory circuitry 43 in a form of a program.

Similarly to the processing circuitry 44 according to the first embodiment, the processing circuitry 44C identifies to which of the devices 22 each of images of a plurality of devices on the X-ray image corresponds in advance. The processing circuitry 44C stores information indicating each of the images of the plurality of devices on the X-ray image and information on ID defined for each of the plurality of devices 22, for example (a "catheter 1" and a "catheter 2", for example) in association in the memory circuitry 43.

The replacement receiving function 81 receives selection of the device to be replaced by the user for the devices included in the first X-ray image. The device to be replaced refers to a device to be removed from the robot arm 21 through replacement in the devices inserted into the object O and included in the first X-ray image. For example, the user instructs the device to be replaced to the processing circuitry of the control device 34 (see medium stage in FIG. 14) through the touch panel of the display input circuit 31 or 32 or the hard key of the remote input circuit 33. The processing circuitry of the control device 34 gives this instruction information on the device to be replaced to the replacement receiving function 81.

The replacement receiving function 81 may receive an input of information on an application of the device and the like by the user. In this case, the replacement receiving function 81 specifies the device 22 to be replaced on the basis of this information on the application and the like.

Similarly to a method of presentation of the information on the current device to be operated according to the second embodiment, the replacement target presenting function 82 presents information on the device to be replaced in the devices included in the first X-ray image to the user of the remote input circuit 33 in collaboration with the processing circuitry of the control device 34.

If the medical image diagnosis system 10 includes a plurality of the remote input circuits 33, the replacement target presenting function 82 only needs to present information on the device to be replaced at least on the display of the display input circuit 32 of the remote input circuit 33 corresponding to the device 22 to be replaced.

The replacement receiving function 81 may receive not the device included in the first X-ray image but the information on the device after replacement. The device after replacement refers to a device to be attached to the robot arm 21 by the replacement. In this case, the memory circuitry 43 only needs to store information such as a product name, a model number, a manufacturer, a shape and the like of the device which is a device candidate after the replacement in a table in advance. In this case, similarly the replacement target presenting function 82 presents information on the device after the replacement to the user of the remote input circuit 33 in collaboration with the processing circuitry of the control device 34.

The replacement receiving function 81 may specify information on replacement timing, the device to be replaced, the device after the replacement and the like in accordance with progress of the manipulation if a workflow of the manipulation is set in advance, for example. In this case, the replacement target presenting function 82 presents information such as the specified replacement timing, the device to be replaced, the device after the replacement and the like to the user.

The medical image diagnosis system 10 according to the fourth embodiment exerts an effect similar to that of the medical image diagnosis system 10 according to the first embodiment and can present the information on the device to be replaced and the information on the device after the replacement to the user. The processing circuitry 44C according to the fourth embodiment may realize the functions 61 to 63 according to the second embodiment, may realize the function 71 according to the third embodiment or may realize all of them. When the function 71 according to the third embodiment is to be realized, the medical image diagnosis system 10 includes the camera 70.

According to at least one of the above-described embodiments, the X-ray diagnosis apparatus is able to display an image identifiably displaying at least a part of the selected device to be operated on an X-ray image. Thus, a user can easily grasp a correspondence between each of the plurality of devices on the X-ray image and each of the plurality of devices 22 of the remote catheter system.

The touch sensors of the display input circuits 31 and 32, and the remote input circuit 33 in the above-described embodiments are examples of the operating circuitry described in the claims. The display 18 and the displays of the display input circuits 31 and 32 in the above-described embodiments are examples of the display described in the claims.

The processing circuitry 44, 44A, 44B, 44C of the image processing device and the processing circuitry of the remote console 30 in the above-described embodiments are examples of the processing circuitry described in the claims.

In addition, the term "processor" used in the explanation in the above-described embodiments, for instance, a circuit such as a dedicated or general-purpose CPU (Central Processing Unit), a dedicated or general-purpose GPU (Graphics Processing Unit), an ASIC (Application Specific Integrated Circuit), a programmable logic device including an SPLD (Simple Programmable Logic Device) and a CPLD (Complex Programmable Logic Device) as examples, and an FPGA (Field Programmable Gate Array). A processor implements various types of functions by reading out programs stored in the memory circuit and executing the programs.

In addition, programs may be directly installed in the circuit of a processor instead of storing programs in the memory circuit. In this case, the processor implements various types of functions by reading out programs stored in its own circuit and executing the programs. Moreover, each function of the processing circuitry may be implemented by processing circuitry configured of a single processor. Further, the processing circuitry may be configured by combining plural processors independent of each other so that each function of the processing circuitry is implemented by causing each processor to execute the corresponding program. When plural processors are provided for the processing circuitry, a memory circuit for storing the programs may be provided for each processor or one memory circuit may collectively store all the programs corresponding to all the processors.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical image diagnosis system, comprising:
   a plurality of devices to be inserted into a body of an object, wherein at least one of the plurality of devices is so constituted that an angle of a distal end portion of the at least one of the plurality of devices is variable;
   operating circuitry configured to operate the at least one of the plurality of devices;
   processing circuitry configured to obtain a plurality of medical images of the object and to specify a device being currently operated among the at least one of the plurality of devices based on movement of the device being currently operated in the plurality of medical images when the device being currently operated is being operated by the operating circuitry; and
   a display configured to identifiably display the device being currently operated by the operating circuitry based on a result of specification by the processing circuitry,
   wherein the processing circuitry is configured to, (1) when a predetermined superimposing condition is satisfied such that the angle of the distal end portion of the device being currently operated changes, cause the display to superimpose an image identifiably displaying an entirety of the specified device being currently operated on the plurality of medical images, and (2) when a predetermined erasing condition is satisfied, erase the image identifiably displaying the entirety of the specified device superimposed on the plurality of medical images.

2. The medical image diagnosis system according to claim 1, wherein the operating circuitry receives a selection of the device being currently operated among the at least one of the plurality of devices.

3. The medical image diagnosis system according to claim 1, wherein
   the operating circuitry includes first operating circuitry which operates a first device among the at least one of the plurality of devices to be inserted into the body of the object and second operating circuitry which operates a second device among the at least one of the plurality of devices to be inserted into the body of the object.

4. The medical image diagnosis system according to claim 3, wherein
   the display is configured to identifiably display the first device operated by the first operating circuitry and the second device operated by the second operating circuitry.

5. The medical image diagnosis system according to claim 1, wherein
   the processing circuitry is configured to specify the device being currently operated based on a result of a subtraction process performed on the plurality of medical images.

6. The medical image diagnosis system according to claim 1, wherein the plurality of medical images is a plurality of X-ray images obtained continuously in a time series.

7. The medical image diagnosis system according to claim 1, wherein
   the processing circuitry is configured to control a state of a device among at least one of the plurality of devices that is not being currently operated based on information on at least either one of movement of the object and a visual line of an operator.

8. The medical image diagnosis system according to claim 1, wherein the processing circuitry is configured to:
   receive selection, from a user, of a device to be replaced of a user among the at least one of the plurality of devices and
   present information on the device to be replaced among the at least one of the plurality of devices.

9. The medical image diagnosis system according to claim 1, wherein the processing circuitry is configured to:
   obtain a movement amount of a bed on which the object is placed;
   acquire a position of the specified device being currently operated on the plurality of medical images after movement of the bed based on the movement amount of the bed; and
   cause an image identifiably displaying an entirety of the specified device being currently operated as to be depicted at a position according to the acquired position on the plurality of medical images.

10. The medical image diagnosis system according to claim 9, wherein
    the movement of the bed includes rotational movement; and
    the processing circuitry is configured to:
       obtain a three-dimensional medical image of the object;
       specify a position in a blood vessel into which the specified device is inserted for each of the blood vessel on the three-dimensional medical image and a blood-vessel shape of the three-dimensional medical image, and specify a three-dimensional coordinate of the specified device;

acquire a position of the specified device on the three-dimensional medical image after the rotational movement of the bed based on a rotational movement amount of the bed; and cause the image identifiably displaying the entirety of the specified device being currently operated so as to be depicted at a position according to the acquired position on the three-dimensional medical image.

11. The medical image diagnosis system according to claim 1, wherein the processing circuitry is configured to:

obtain a movement amount of an X-ray irradiation shaft of an imaging system which carries out imaging of the plurality of medical images;

acquire a position of the specified device on the plurality of medical images after movement of the X-ray irradiation shaft based on the movement amount of the X-ray irradiation shaft; and cause an image identifiably displaying an entirety of the specified device being currently operated so as to be depicted at a position according to the acquired position on the plurality of medical images.

12. The medical image diagnosis system according to claim 11, wherein the movement of the X-ray irradiation shaft includes rotational movement; and the processing circuitry is configured to:

obtain a three-dimensional medical image of the object;

specify a position in a blood vessel into which the specified device is inserted for each of the blood vessel on the three-dimensional medical image and a blood-vessel shape of the three-dimensional medical image, and specify a three-dimensional coordinate of the specified device;

acquire a position of the specified device on the three-dimensional medical image after the rotational movement of the X-ray irradiation shaft based on a rotational movement amount of the X-ray irradiation shaft; and cause the image identifiably displaying the entirety of the specified device being currently operated so as to be depicted at a position according to the acquired position on the three-dimensional medical image.

13. The medical image diagnosis system according to claim 12, wherein the processing circuitry is configured to:

obtain information on a feeding movement amount of the device being currently operated from the operating circuitry;

acquire a position of the specified device on the plurality of medical images after the feeding movement of the device based on the information on the feeding movement amount of the device included in the plurality of medical images; and cause the image identifiably displaying entirety of the specified device so as to be depicted at a position according to the acquired position on the plurality of medical images.

14. The medical image diagnosis system according to claim 1, further comprising:

a system that includes the operating circuitry and is configured to remotely control the at least one of the plurality of devices.

15. The medical image diagnosis system according to claim 14, wherein the processing circuitry is configured to collaborate with processing circuitry of the system for remote control of the device and present information on the device being currently operated by the operating circuitry to a user of the system for remote control of the device.

16. The medical image diagnosis system according to claim 15, wherein the processing circuitry is configured to cause the display to superimpose an image identifiably displaying an entirety of a device selected by the user on the plurality of medical images.

17. An X-ray diagnosis apparatus, comprising:

an X-ray source and an X-ray detector to perform X-ray imaging of an object; and processing circuitry configured to:

obtain a plurality of medical images of the object, wherein a plurality of devices are inserted into a body of the object and at least one of the plurality of devices is so constituted that an angle of a distal end portion of the at least one of the plurality of devices is variable;

specify a device being currently operated among the plurality of devices based on movement of the device being currently operated in the plurality of medical images when the device being currently operated is being operated by operating circuitry configured to operate at least one of the plurality of devices;

cause a display to identifiably display the device being currently operated by the operating circuitry based on a result of specification by the processing circuitry, when a predetermined superimposing condition is satisfied such that the angle of the distal end portion of the device being currently operated changes, cause the display to superimpose an image identifiably displaying an entirety of the specified device being currently operated on the plurality of medical images, and when a predetermined erasing condition is satisfied, erase the image identifiably displaying the entirety of the specified device superimposed on the plurality of medical images.

* * * * *